(12) United States Patent
Juvinall

(10) Patent No.: US 6,175,107 B1
(45) Date of Patent: Jan. 16, 2001

(54) INSPECTION OF CONTAINERS EMPLOYING A SINGLE AREA ARRAY SENSOR AND ALTERNATELY STROBED LIGHT SOURCES

(75) Inventor: John W. Juvinall, Ottawa Lake, MI (US)

(73) Assignee: Owens-Brockway Glass Container Inc., Toledo, OH (US)

( * ) Notice: Under 35 U.S.C. 154(b), the term of this patent shall be extended for 0 days.

(21) Appl. No.: 09/085,228

(22) Filed: May 27, 1998

(51) Int. Cl.⁷ .................................................... G01N 21/00
(52) U.S. Cl. .................................. 250/223 B; 356/239.4; 356/240.1
(58) Field of Search .......................... 250/223 B, 223 R; 356/240.1, 237.1, 239.1, 239.2, 239.4, 428; 209/524, 525, 526

(56) References Cited

U.S. PATENT DOCUMENTS

| | | |
|---|---|---|
| 4,305,658 | 12/1981 | Yoshida . |
| 4,380,026 | 4/1983 | Kubota . |
| 4,579,227 | 4/1986 | Miller . |
| 4,650,326 | 3/1987 | Nagamine et al. . |
| 4,794,453 | 12/1988 | Gnuechtel et al. . |
| 4,811,251 | 3/1989 | Minato . |
| 4,896,211 | 1/1990 | Hunt et al. . |
| 4,945,228 | 7/1990 | Juvinall et al. . |
| 4,958,223 | 9/1990 | Juvinall et al. . |
| 5,020,908 | 6/1991 | Hermann . |
| 5,305,391 | 4/1994 | Gomibuchi . |
| 5,489,987 | 2/1996 | Ringlien . |
| 5,581,074 | 12/1996 | Yoshida . |
| 5,610,391 | 3/1997 | Ringlien . |
| 5,617,204 | 4/1997 | Hinata . |
| 5,661,294 | 8/1997 | Buchmann et al. . |
| 5,896,195 | * 4/1999 | Juvinall et al. ................... 356/240.1 |

FOREIGN PATENT DOCUMENTS

| | | |
|---|---|---|
| 0222959 | 5/1987 | (EP) . |
| 0731350 | 9/1996 | (EP) . |
| 0878705 | 11/1998 | (EP) . |

* cited by examiner

Primary Examiner—John R. Lee

(57) ABSTRACT

An apparatus for inspecting a container includes a first light source for generating light energy of a first character and directing the light energy onto a predetermined portion of a container under inspection, and a second light source for generating light energy of a second character different from the first character and directing such light energy onto the same predetermined portion of the container under inspection. An area array light sensor is disposed to receive a two-dimensional image of the portion of the container illuminated by the first and second light sources. The first and second light sources are sequentially and alternately strobed, and first and second two-dimensional images of the container portion under inspection are downloaded from the sensor. Commercial variations that affect optical properties of the containers are identified by comparing the first and second two-dimensional images from the respective light sources scanned from the sensor. The sensor preferably includes facility for scanning two-dimensional images in sequential frames, and the first and second images are obtained by scanning sequential frames from the sensor during which the first and second light sources are alternately strobed.

29 Claims, 4 Drawing Sheets

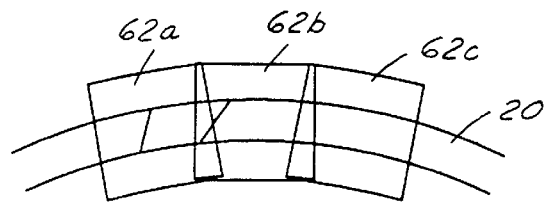
FIG. 5A
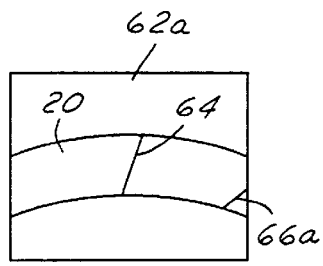 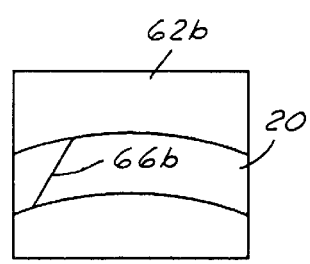 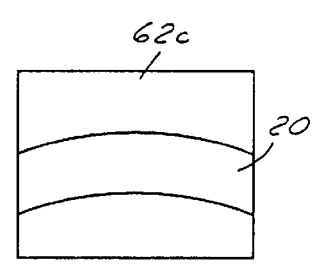
FIG. 5B          FIG. 5C          FIG. 5D
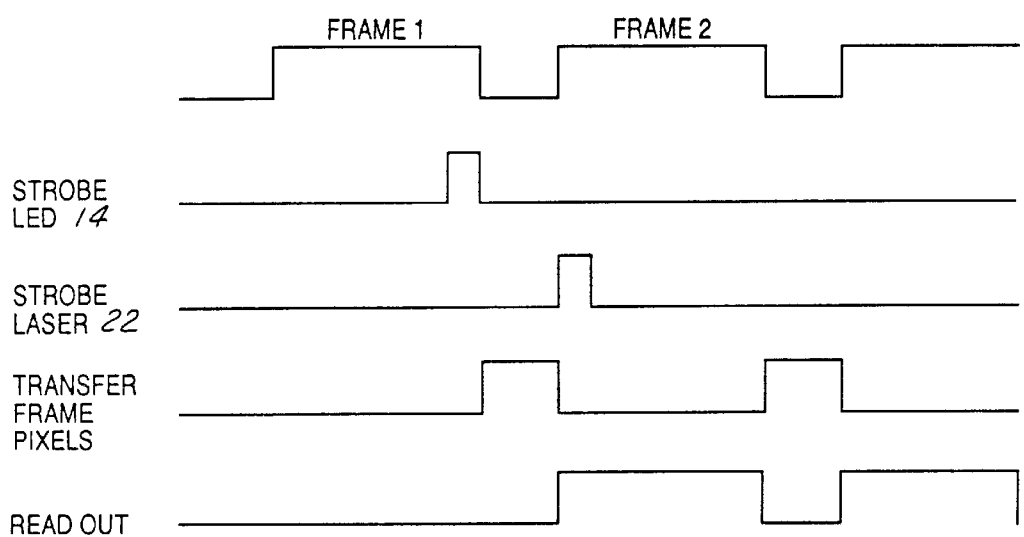
FIG. 6

INSPECTION OF CONTAINERS EMPLOYING A SINGLE AREA ARRAY SENSOR AND ALTERNATELY STROBED LIGHT SOURCES

The present invention is directed to inspection of containers for commercial variations that affect the optical properties of the containers, and more particularly to a method and apparatus for inspecting containers based upon comparison of two-dimensional images of the inspected portions of the container.

BACKGROUND AND OBJECTS OF THE INVENTION

In the manufacture of containers such as glass bottles and jugs, various types of anomalies can occur in the sidewalls, heels, bottoms, shoulders, necks and/or finishes of the containers. These anomalies, termed "commercial variations" in the art, can affect commercial acceptability of the containers. It has been proposed to employ electro-optical inspection techniques for detecting commercial variations that affect the optical properties of the containers. The basic principle is that a light source is positioned to direct light energy onto the container, and a camera is positioned to receive an image of the portion(s) of the container illuminated by the light source. The light source may be of uniform intensity, or may be configured to have an intensity that varies across one dimension of the light source. Commercial variations in the portion of the container illuminated by the light source are detected as a function of light intensity in the image of the illuminated container received and stored at the camera.

U.S. Pat. No. 4,945,228, assigned to the assignee hereof, discloses an apparatus for inspecting the sealing surface of a container finish, which includes a light source positioned to direct light energy onto the container sealing surface as the container is held in stationary position and rotated about its central axis. A camera, which includes a linear array or matrix (area) array of light sensitive elements, is positioned and oriented with respect to the container axis of rotation to receive light energy reflected from the sealing surface, with the camera having an effective field of view limited to an angular portion less than the entire circumference of the container sealing surface. The camera array is scanned at increments of container rotation to develop information indicative of intensity of light at each array element as a function of such increments, and commercial variations at the container sealing surface are detected as a function of such information. The apparatus so disclosed is well adapted to detect commercial variations that affect reflectivity of the container sealing surface, such as line-over-finish variations, blisters, stones and a dirty container finish.

U.S. Pat. No. 5,489,987, also assigned to the assignee hereof, discloses an apparatus for inspecting the sealing surface area of a container, which includes a light source positioned to direct a narrow beam of light energy at an acute angle onto the sealing surface area of a container as the container is rotated about its central axis. A light sensor is disposed to receive the narrow beam of light energy reflected from the sealing surface area, and provides an output signal that varies as a function of position of incidence of the reflected light beam on the sensor. That is, the reflected light beam is incident on the sensor at a position that varies with height or level of the sealing surface with respect to the light source and sensor, and the sensor is characterized by providing an electrical output signal that varies as a function of position of incidence of the reflected light beam on the sensor. Variations in height at the sealing surface area are detected as a function of the sensor output signal. In one embodiment, light source/sensor pairs are disposed on diametrically opposed sides of the container axis, and warp, dip and/or cock at the sealing surface of the container is detected as a combined function of variations in position of incidence of the reflected light beams on the sensors as the container rotates.

Copending U.S. application Ser. No. 08/856,829, also assigned to the assignee hereof, now U.S. Pat. No. 5,896,195 discloses a method and apparatus for inspecting the sealing surface of a container. In one embodiment, first and second light sources direct light energy onto the sealing surface of a container from differing angles with respect to the container axis and the nominal plane of the sealing surface. Light energy reflected by the sealing surface area of the container from the first and second light sources is directed onto an area array sensor in such a way that the sensor effectively views the container sealing surface area from two differing angles corresponding to the angles of illumination from the light sources. The differing light sources are of differing structure or nature for illuminating the sealing surface with light having differing properties as well as differing illumination angles for detecting differing physical and/or dimensional characteristics of the container sealing surface. The light sources are alternately energized, and the area array sensor is scanned to develop sequential two-dimensional images indicative of differing sealing surface characteristics. Inaccuracies can arise associated both with container movement between sequential frame scans and ambient light incident on the area array sensor during each image frame. When the subject matter of this copending application is implemented at the so-called cold end of the container manufacturing process, at which the container is held in stationary position and rotated about its central axis, the container will not only undergo finite rotation between sequential frame scans, but also may wobble laterally between sequential frame scans. Likewise, when implemented at the so-called hot end of the manufacturing process, at which a container is moved in a direction transverse to its axis beneath the inspection apparatus, the container sealing surface (or other area being inspected) will move a finite distance between sequential frame scans. It is important in obtaining reliable inspection information to minimize the effects of both container movement and ambient light during the inspection operation. It is a general object of the present invention to provide a method and apparatus for container inspection in which one or both of these objectives are accomplished.

SUMMARY OF THE INVENTION

Apparatus for inspecting a container in accordance with a presently preferred embodiment of the invention includes a first light source for generating light energy of a first character and directing the light energy onto a predetermined portion of a container under inspection, and a second light source for generating light energy of a second character different from the first character and directing such light energy onto the same predetermined portion of the container under inspection. An area array light sensor is disposed to receive a two-dimensional image of the portion of the container illuminated by the first and second light sources. The first and second light sources are sequentially and alternately energized, and first and second two-dimensional images of the container portion under inspection are downloaded from the sensor. Commercial variations that affect optical properties of the containers are identified by comparing the first and second two-dimensional images from the respective light sources scanned from the sensor. The sensor preferably includes facility for scanning two-dimensional images in sequential frames, and the first and second images are obtained by scanning sequential frames from the sensor during which the first and second light sources are alternately energized.

The first and second light sources are strobed during the associated scan frames at the area array sensor. In some embodiments of the invention, the first light source is strobed at the end of a first scan frame and the second light source is strobed at the beginning of a second scan frame, which minimizes the effects of container movement between frames. In other embodiments of the invention, the integration of light energy at the individual pixel elements of the sensor is controlled during the scan frames to minimize effects of ambient light. The first light source is strobed at the end of the first frame, and the second light source may be strobed at the end of the second frame to minimize the effects of ambient light. Alternatively, the second light source may be strobed at the beginning of the second frame to minimize the effects of container movement, and the pixel data may be clock off of the sensor during the second frame so that the effects of ambient light are "smeared" throughout the second frame image. The effects of such smeared ambient light may be minimized by employing so-called edge-magnitude detection techniques to obtain the two-dimensional image of the second scan frame as a function of a comparison between the same pixel element signals in adjacent scanned lines.

A method of inspecting a container for variations that affect commercial acceptability of the container in accordance with another aspect of the invention includes the steps of alternately directing first and second light energies of differing character onto a portion of the container, obtaining first and second two-dimensional images of the portion of the container during illumination by the first and second light energies respectively, and detecting commercial variations at the container that affect optical properties of the container by comparison of the first and second images. The first and second light energies preferably are directed alternately onto a single area array sensor to develop the two-dimensional images of the illuminated portion of the container and scanning the two-dimensional images from the sensor. The two-dimensional images are compared to detect commercial variations at the container by overlapping the images, preferably by employing one of the images to predict areas of possible occurrence of variations in the other of the images.

In the preferred embodiments of this aspect of the invention, the first and second two-dimensional images of the illuminated portion of the container are obtained by controlling the sensor in sequential scan frames of equal time duration, directing the first and second light energies onto the container during sequential first and second associated scan frames at the sensor, and scanning the sensor during the first and second scan frames to obtain the desired two-dimensional images of the illuminated portion of the container. Most preferably, the first light source is strobed to direct light energy onto the container and sensor during a small portion of the first scan frame, and the second light source is strobed to direct light energy onto the container and sensor during a small portion of the second scan frame. The first light source preferably is strobed at the end of each first scan frame, and the second light source may be strobed at either the beginning or the end of each second scan frame depending upon the frame control and scanning technique employed. The integration time of the first frame can be limited to the short strobe time of the first light source, thereby limiting the integration of ambient light in the first frame. Most preferably, the second light source is strobed at the beginning of each second scan frame, and the sensor is controlled to integrate light energy from the second light source during the entirety of the second scan frame. The sensor is scanned during the second scan frame by pixel line at the sensor, so that the effects of ambient light during scanning of the second frame are smeared throughout sequential pixel lines scanned from the sensor. By employing edge-magnitude detection techniques, in which each pixel signal in each line scanned from the sensor is compared to the same pixel signal from the next line scanned from the sensor, the effects of ambient light smearing are minimized.

BRIEF DESCRIPTION OF THE DRAWINGS

The invention, together with additional objects, features and advantages thereof, will be best understood from the following description, the appended claims and the accompanying drawings in which:

FIGS. 5A, 5B, 5C and 5D illustrate respective two-dimensional images of the inspected portion of the container in FIG. 1, and are useful in describing operation of the invention; and FIGS. 6, 7 and 8 are timing diagrams that illustrate scanning of the camera in FIG. 1 in accordance with three respective embodiments of the invention.

DETAILED DESCRIPTION OF PREFERRED EMBODIMENTS

The disclosure of above-noted copending U.S. application Ser. No. 08/856,829 is incorporated herein by reference. The disclosure above-noted of U.S. Pat. No. 4,958,223 is incorporated herein by reference.

Figure 1:
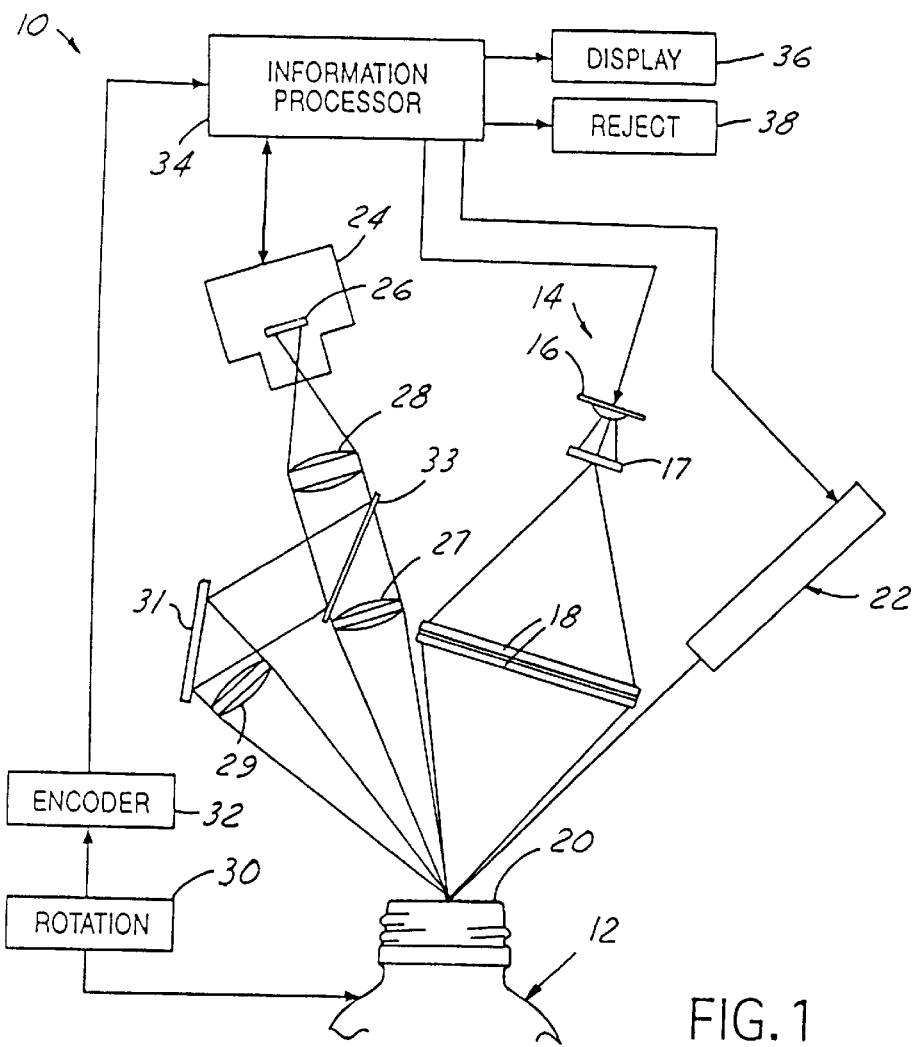
FIG. 1 is a schematic diagram of apparatus for inspecting the sealing surface of containers in accordance with one presently preferred embodiment of the invention.

FIG. 1 illustrates an apparatus 10 for inspecting a container 12 in accordance with one presently preferred embodiment of the invention. A first light source 14, such as an LED transmitter 16, is disposed above container 12 and oriented to direct light energy through a diffuser 17 and a set of fresnel lenses 18 downwardly onto the sealing surface 20 of container 12. A second light source 22, such as a laser, is also disposed above container 12 and oriented to direct a narrow line-shaped light beam downwardly onto sealing surface 20 at a position coincident with the light beam from LED 16. The diffuse light from LED light source 14 illuminates the entire radial and a portion of the circumferential dimension of the sealing surface, while the line-shaped light beam from laser light source 22 is oriented laterally or radially of the sealing surface. A camera 24 has an area array sensor 26 onto which light energy reflected from sealing surface 20 is focused by lenses 27, 28. Camera 24 is positioned above sealing surface 20 and oriented to receive light energy reflected by the sealing surface from LED light source 14. That is, camera 24 and sensor 26 are oriented with respect to LED light source 14 so that light energy from LED 16 is normally reflected by sealing surface 20 at the nominal planar position of the sealing surface through lenses 27, 28 onto sensor 26. On the other hand, laser light source 22 is oriented at a more acute angle to sealing surface 20 so that light energy incident therefrom onto sealing surface 20 is reflected onto sensor 26 through lenses 28, 29, a mirror 31 and a beamsplitter 33 disposed between lenses 27, 28.

A conveyor, typically including a starwheel and a slide plate, is disposed and connected to a source of containers 12 so as to move the successive containers through an arcuate path and bring the successive containers into position at apparatus 10 between light sources 14, 22 and camera 24. Apparatus 10 is preferably disposed at one station of a starwheel-conveyor container inspection system of the type in U.S. Pat. Nos. 4,230,319 and 4,378,493, the disclosures of which are incorporated herein by reference for purposes of background. Successive containers 12 are thus held stationary beneath light sources 14, 22 and camera 24, and are rotated by a drive roller 30 or the lie about the central axis of each container. An encoder 32 is coupled to the container rotation mechanism to provide signals indicative of increments of container rotation. Such increments may comprise either fixed angular increments of rotation, or fixed time increments of rotation at constant velocity. An information processor 34 is coupled to encoder 32, camera 24 and light sources 14, 22 for controlling operation of light sources 14, 22 and scanning of camera 24 as will be described. Information processor 34 is also coupled to a display 36 for providing alphanumeric and/or graphic display of container inspection information to an operator, and to a reject mechanism 38 for removing from the conveyor system containers that do not pass inspection.

The embodiment of the invention illustrated in FIG. 1 is particularly well suited for implementation at the so-called cold end of a glass manufacturing system after the containers have passed through an annealing lehr, and at which the containers are sufficiently cool to be handled by a starwheel conveyor and drive roller. The principles of the invention may also be implemented at the so-called hot end of the manufacturing system between the glass manufacturing machine and the annealing lehr. Glass containers manufactured in an individual section machine, for example, are transferred onto a linear conveyor 40 (FIG. 2), on which the containers are conveyed in-line from the manufacturing machine to the annealing lehr. Conveyor 40 is coupled to a conveyor drive mechanism 42, which may provide to information processor 34 (FIG. 1) signals indicative of increments of container motion on the conveyor. Apparatus 10 in FIG. 1 may be disposed above conveyor 40 so that a container 12 on conveyor 40 passes beneath the light sources and camera for inspection of the container sealing surface as will be described. In this implementation, the camera may be scanned at increments of linear conveyor motion transverse to the axis of the container. There are a number of camera/scan options that can be employed in applications in which the container translates rather than rotates beneath the light sources. For example, a high resolution camera can be employed to obtain a pair of images of the full finish. A rectangular area array sensor can be employed to obtain multiple "slices" of the finish as it translates beneath the inspection head. A low resolution camera can be employed in combination with servo-driven mirrors to view the complete finish circumference as the container translates beneath the inspection head. The containers are placed onto conveyor 40 by the manufacturing machine in a predetermined and continuous sequence according to machine mold and section. Information processor 34 may provide information indicative of commercial variations at the container sealing surface and/or automatically implement adjustments or corrections at the manufacturing machine to correct any noted commercial variations.

Figure 3:
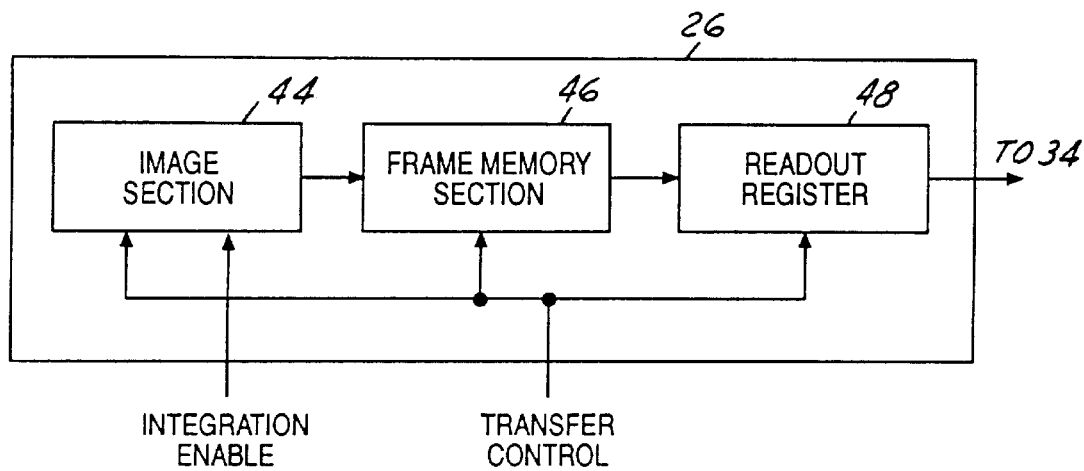
FIG. 3 is a functional bock diagram of a frame-transfer CCD sensor that may be employed in the camera of FIG. 1.

Area array sensor 26 of camera 24 comprises a plurality of CCD picture elements or pixels disposed in a rectangular row-and-column array. The pixel elements are characterized by the fact that they are responsive to incident light energy to provide an electrical signal indicative of the total quantum of light energy incident on the pixel element. In other words, when enabled to operate, each pixel element effectively integrates the quantity of light energy incident thereon. The sensor in accordance with the present invention preferably comprises a frame transfer CCD sensor. In general, this type of CCD area array sensor comprises an image section containing the multiplicity of pixel elements, a memory section into which the pixel element signals may be transferred, and a readout register through which the pixel element signals in the memory section are transported for transfer off of the sensor. FIG. 3 illustrates a frame transfer sensor 26, which includes an image section 44 containing the array of pixel elements. Image section 44 is connected to a frame memory section 46, which in turn is connected to a readout register 48 for transporting image data to information processor 34 (FIG. 1). Control signals from information processor 34 for controlling operation of sensor 26 include an integration enable input to image section 44, and transfer control inputs to image section 44, frame memory section 46 and readout register 48. In general, frame transfer sensor 26 transfers a frame one line at a time. Thus, a line or row of pixel signals is transferred from image section 44 to frame memory section 46, while a line or row of signals in frame memory section 46 is transferred to readout register. This process continues until an entire frame is transferred. Frame transfer sensor 26 is itself well known in the art.

Figure 4A:
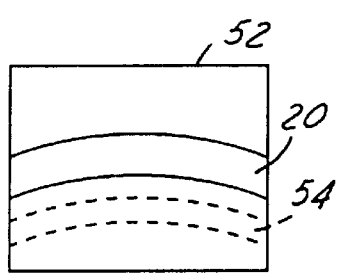
FIGS. 4A, 4B and 4C illustrate respective two-dimensional images of the container under inspection, and are useful in describing operation of the invention.
Figure 4B:
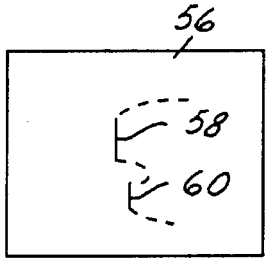
Figure 4C:
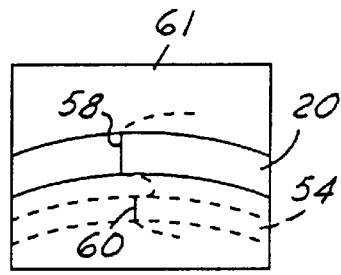

In general, information processor 32 (FIG. 1) alternately energizes LED light source 14 and laser light source 20, and scans associated two-dimensional images of the container sealing surface from area array sensor 26 of camera 24. By comparing the image at the camera from LED light source 14 to the image at the camera from laser light source 22, useful information can be obtained. For example, referring to FIGS. 4A–4C, information processor 34 may obtain from camera 24 a two-dimensional image 52 of the segment of the sealing surface 20 illuminated by LED light source 14. Employing this image 52, information processor 34 determines the position of sealing surface 20, and predicts a position 54 for any wire edge or overpress that may be disposed in the step-down area inside of the sealing surface. Information processor 34 then analyzes the image 56 scanned from sensor 26 during illumination by laser light source 22, from which two areas of reflection 58, 60 are noted. Reflection 58 is from the top of sealing surface 20, while reflection 60 is from the step-down area radially immediately inside of the sealing surface. By analytically overlapping the images 52, 56, and thereby developing a composite image 62, information processor 34 may determine that the reflection 58 is associated with sealing surface 20, while reflection 60 is in the step-down area 54 within which a wire edge or overpress may be expected. Thus, reflection 60, being within the wire edge or overpress area 54, may be compared by position with respect to reflection 58 to determine whether the wire edge is of sufficient height to constitute an overpress condition, necessitating rejection of the container and possible corrective action at the manufacturing machine mold of origin. This comparison may be accomplished automatically within information processor 34 by means of a pixel-by-pixel comparison of images 52, 56, or may be accomplished manually by an operator at display 36 at which composite image 62 is displayed.

FIGS. 5A–5D illustrate three sequential composite images 62a, 62b, 62c with respect to a container sealing surface 20. That is, information processor 34 (FIG. 1) energizes each light source 14, 22, and scans sensor 26 as each light source is energized, to obtaining a composite image 62 at each increment of container rotation. FIGS. 5A–5D illustrate three such composite images 62a, 62b, 62c at three increments of container rotation. In each image, sealing surface 20 is clearly illustrated as illuminated by LED light source 14. Within image 62a, a line-over-finish variation is indicated at 64, and a second line-over-finish variation is indicated at 66a. However, because image 62a only captured a portion of the line-over-finish variation 66a, this variation might be missed or ignored at the image processor. The full line-over-finish variation is shown at 66b in image 62b. Thus, by controlling operation of light sources 14, 22 and scanning of camera 24 so as to obtain overlapping images 62a, 62b, 62c, a line-over-finish variation 66b is detected which might otherwise be missed because it lies adjacent to the boundary between sequential frames. Other light sources, such as a crizzle LED, may be employed in combination with light sources 14, 22, as disclosed in the above-referenced copending application.

Figure 2:
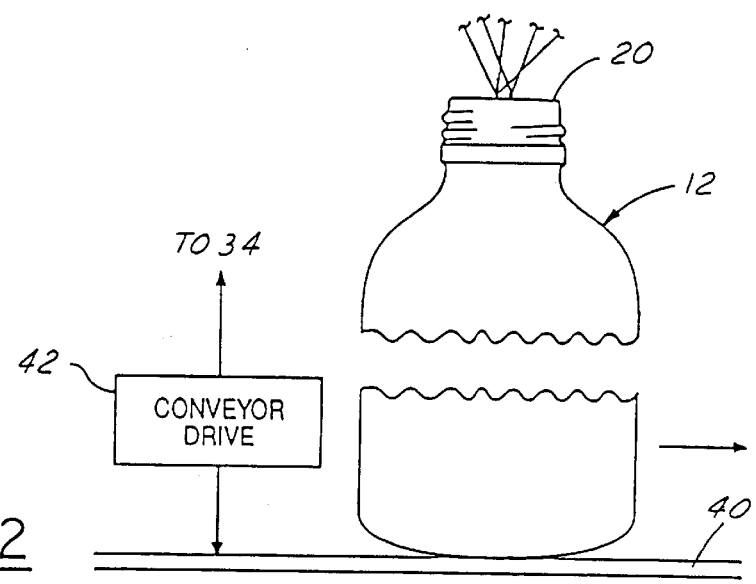
FIG. 2 is a fragmentary schematic diagram that illustrates a modification to the embodiment of FIG. 1.

Thus, in order to obtain two different images from the two light sources, one light source illuminates the container during one camera frame, and the other light source illuminates the container during the next camera frame. The camera image frames are of equal time duration. This sequence is repeated as the container is rotated (FIG. 1) or translated (FIG. 2). The pixel data accumulated at the camera sensor may be downloaded from the pixel array, whereupon the individual pixels can integrate new image data. The normal method of taking two consecutive images with a single camera is to strobe the two light sources in two adjacent camera frames, and therefore the acquisition of the two images would be separated by one frame time. In a high-speed 128×128 area array sensor, the camera may be clocked at 16 MHz, so that the time allocated for each frame would be 1 ms. For an inspection machine running at 360 bottles per minute (with 50% of the time being used for inspection and each bottle rotating 1.5 times per inspection period), and with bottles having a one-inch diameter finish, the finish will rotate about 0.060 inches in 1 ms. If the bottle handling is less than optimum and the bottle moves radially one part for two parts of circumferential motion over a short distance, then the finish would move radially 0.030 inches in each 1 ms frame time. This could easily move sealing surface reflection 58 (FIGS. 4B and 4C) into wire edge area 54, for example, causing a false detection of a wire edge or overpress. Furthermore, acceptance and integration of ambient light over a 1 ms frame time would yield an undesirable signal-to-noise ratio at the camera. It is preferable to strobe light sources 14, 22 for a very short time duration, such as on the order of 15 microseconds. The container will only rotate about 0.001 inch during this time, which reduces motion blur. Furthermore, integration time can be limited to the 15 microsecond duration of the strobing of each light source.

FIG. 6 illustrates one light source and frame scan control technique that can be employed. LED light source 14 is strobed at the end of frame 1 and laser light source 22 is strobed at the beginning of frame 2. Pixel data is transferred from the image section to the memory section during the inter-frame periods, and is downloaded from the sensor readout register to the image processor during the subsequent frame. (It will be appreciated, of course, that "frame 1" and "frame 2" in FIG. 6, and FIGS. 7–8, alternate continuously during operation. Thus, frame 1 and frame 2 in FIG. 6 may be associated with composite image 62a in FIG. 5A, for example. The next frame 1–frame 2 sequence would then be associated with composite image 62b, etc.) By strobing LED light source 14 at the end of frame 1 and laser light source 22 at the beginning frame 2, the time delay between illuminations by the light sources is minimized, so that the container will not have moved significantly between obtaining the two-dimensional images associated with frames 1 and 2. This technique minimizes the problem of container movement between frame scans, but does not address the problem of ambient light falling on the camera sensors. The pixels in sensor 26 will receive and integrate ambient light during the entirety of both frames 1 and 2 in FIG. 6, and data associated with this ambient light will be transferred to the image processor.

Figure 7:
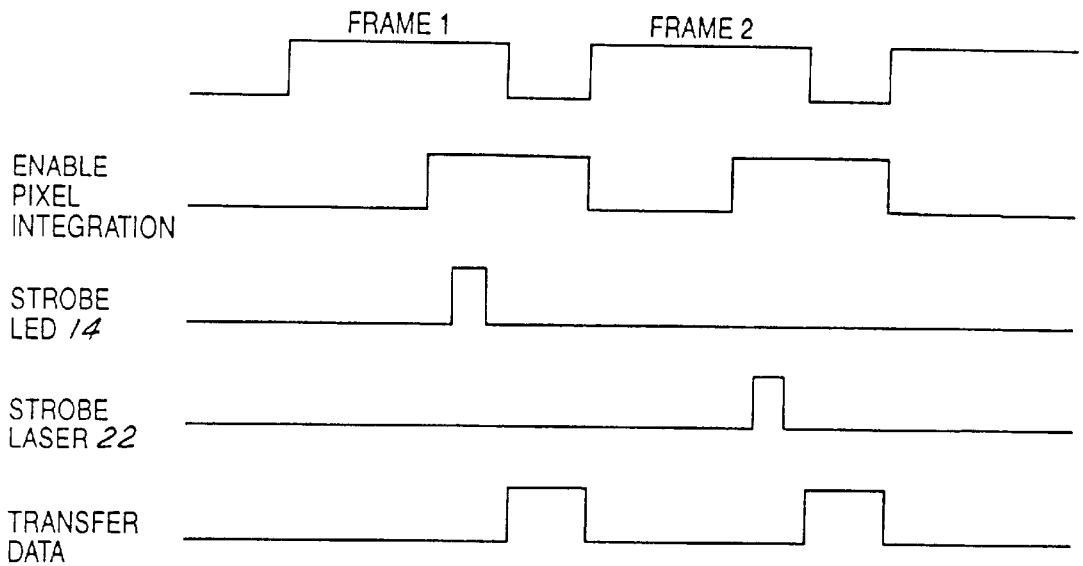
Figure 8:
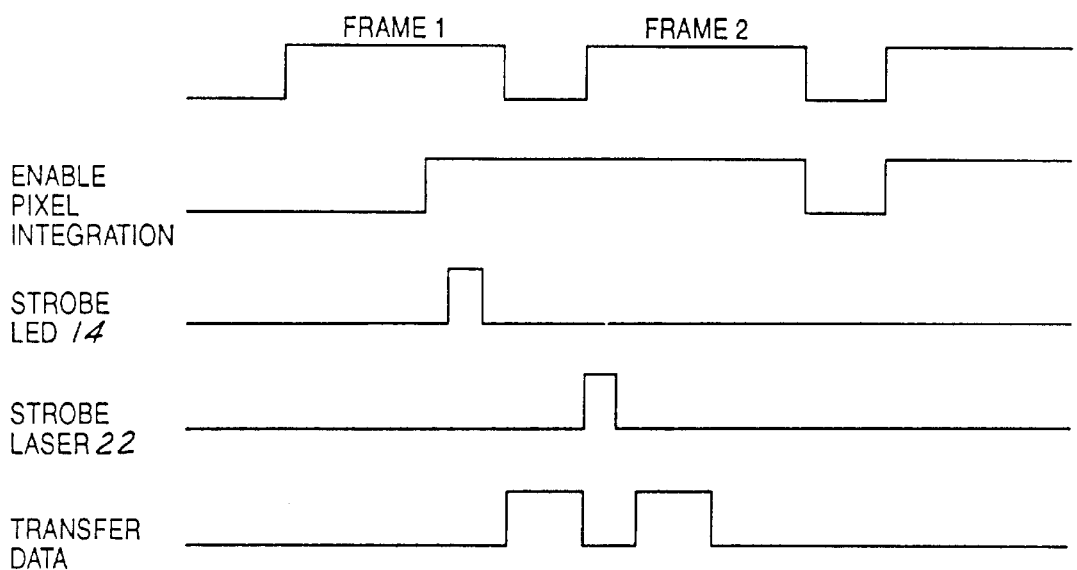

FIGS. 7 and 8 illustrate light source control and frame scanning techniques that make use of an ability available on many area array sensors to enable integration at the individual pixel elements through an integration enable control signal from information processor 34. Thus, the pixel elements in the sensor array will be enabled to integrate light incident thereon during the duration of the enable signal, but must transfer data during the enable signal or the pixel data will be lost. When not enabled, the pixels are effectively grounded. FIG. 7 illustrates one technique making use of this feature. Pixel integration is enabled at the end of frame 1 and at the end of frame 2. LED light source 14 is strobed at the end of frame 1, and laser light source 22 is strobed at the end of frame 2. Pixel data is transferred during the inter-frame periods immediately following frames 1 and 2, and is downloaded through the readout register during the succeeding frame period. The technique illustrated in FIG. 7 effectively addresses the problem of ambient light incident on the pixels by enabling integration at the pixel elements only at the time the associated light source is strobed. However, significant movement of the container area under inspection will take place between the image scan periods at the ends of frames 1 and 2.

FIG. 8 illustrates a light source and frame scan control technique that is currently preferred. Integration of pixel data is enabled at the end of frame 1, during which time LED light source 14 is strobed as previously described. The pixel data is then downloaded during the inter-frame period between frame 1 and frame 2. Accumulation of ambient light during frame 1 is thereby minimized. Integration of pixel data is again enabled at the onset of frame 2, and laser light source 22 is strobed at the beginning of frame 2. This minimizes the effect of motion at the container between the times that the light sources are strobed. At this point, both images from source 14 and source 22 are entirely on sensor 26 at the same time. Data transfer is begun immediately after the laser light source is strobed. However, integration must remain enabled for the period of data transfer from image section 44 to store section 46 or 50 (FIGS. 3A and 3B) so that this data will not be lost. This allows some ambient light to enter frame 2 during the time that the pixel element data is being clocked off of the area array sensor. Thus, data (from frame 1) is being clocked off the image section of the sensor at the same time as data (from frame 2) is being clocked out of the readout register. The image section of the sensor will continue to integrate light until it is clocked into the store section. The first line clocked into the store section will have very short integration time. However, the last line clocked into the store section will have a full frame of ambient light integration time. This has the effect of spreading or "smearing" ambient light over the entire frame. The last line of image data integrates first at the top of the image, and continues to integrate ambient light as the data is tranferred one line at a time in the image section of the array. The data line is moving through the image section of the array throughout the integration time. The line of data is integrating different ambient light at each point in the image, and is therefore effectively "smearing" the image of ambient light. The image from the strobed light source is not smeared. In theory, this improves the integration of ambient light by an average factor of two. However, in practice, the ambient light when the camera is looking at a container is not uniform across the full image. If the ambient light is centered in the frame and is one-tenth of the full height, then any pixel line at most will be in front of this ambient image on the array for only one-tenth of the total frame time, reducing the maximum amplitude by a factor of ten. The ambient light thus is effectively zero at the first line scanned off of the image section, and at the full one-tenth amplitude at the last line scanned off of the image section. It is preferred to employ edge magnitude detection techniques for developing each scan image. This technique involves comparison of each pixel element data of each line with the data from the corresponding pixel in the preceding line, and entry of image data as a function of the difference therebetween. The comparison threshold can be set to accommodate ambient light smearing, so that only a true image edge will be detected. This light control and frame scanning technique takes advantage of the architecture of conventionally available and inexpensive CCD sensors and cameras, although the clocking logic in the camera must be modified as described.

What is claimed is:

1. A method of inspecting a container for variations that affect commercial acceptability of the container, comprising the steps of:

(a) alternately directing first and second light energies of different character into a portion of the container, (b) obtaining first and second two-dimensional images of the portion of the container illuminated in said step (a) during illumination by said first and second light energies respectively, and (c) detecting commercial variations at the container that affect optical properties of the container by comparison of said first and second images to each other, wherein said step (b) comprises the steps of: (b1) directing said first and second light energies alternately into a single area array sensor to develop two-dimensional images of the illuminated portion of the container at said sensor, and (b2) scanning said two-dimensional images from said sensor, and wherein said step (c) comprises the step of overlapping said images.

2. The method set forth in claim 1 wherein said step of overlapping said images is carried out by employing one of said images to predict areas of occurrence of variations in the other of said images.

3. The method set forth in claim 1 wherein said step (b2) is carried by: (b2a) controlling said sensor in sequential scan frames of equal time duration, (b2b) directing said first and second light energies into the container during sequential first and second scan frames at said sensor, and (b2c) scanning said sensor during said first and second scan frames to obtain said two-dimensional images.

4. The method set forth in claim 1 for inspecting a sealing surface of the container wherein said first light source is such as to obtain at said sensor a two-dimensional image of light energy reflected from the sealing surface against a dark background, and said second light source is such as to obtain at said sensor a two-dimensional image of light energy reflected from high points at said sealing surface against a dark background.

5. The method set forth in claim 1 comprising the additional step of (d) moving the container relative to said light source and said sensor, and wherein said step (b) is carried out at increments of container motion.

6. The method set forth in claim 5 wherein said step (d) comprises the step of rotating the container about its axis.

7. The method set forth in claim 5 wherein said step (d) comprises the step of moving the container in a direction transverse to its axis.

8. Apparatus for inspecting a container that comprises:

a first light source for generating light energy of a first character, including means for directing said light energy from said first source onto a predetermined portion of a container under inspection, a second light source for generating light energy of a second character different from said first character, including means for directing said light energy from said second source into the same predetermined portion of the container under inspection, an area array light sensor disposed to receive a two-dimensional image of the said portion of the container illuminated by said first and second light sources, means for sequentially and alternately energizing said first and second light sources, and downloading from said sensor alternate first and second two-dimensional images of the container portion as illuminated by said first and second light sources respectively, and means for comparing said first and second two-dimensional images to identify commercial variations that affect optical characteristics of the container, wherein said sensor includes means for scanning two-dimensional images thereon in sequential frames, and wherein said first and second images are obtained by scanning sequential frames from said sensor during which said first and second light sources are respectively alternately illuminated.

9. The apparatus set forth in claim 8 further comprising means for strobing said first light source during associated first frames at said sensor, and means for strobing said second light source during associated second frames at said sensor.

10. The apparatus set forth in claim 9 wherein said first light source is strobed at an end of said first frame and said second light source is strobed at a beginning of said second frame.

11. The apparatus set forth in claim 9 wherein said area array sensor has a plurality of individual sensor pixels adapted to integrate light energy incident thereon and to provide pixel signals as a function of said integrated light energy, and wherein said apparatus further comprises means for controlling pixel integration during at least one of said first and second frames so as to reduce effects of ambient light during pixel integration.

12. The apparatus set forth in claim 11 wherein said first light source is strobed at an end of said first frame, and said sensor is controlled to integrate light energy from said first source at the end of said first frame.

13. The apparatus set forth in claim 12 wherein said second light source is strobed at an end of said second frame, and said sensor is controlled to integrate light energy from said second source at the end of said second frame.

14. The apparatus set forth in claim 13 wherein said second light source is strobed at a beginning of said second frame, and said sensor is controlled to integrate light energy from said second source during the entirety of said second frame.

15. The apparatus set forth in claim 14 wherein said pixels are disposed in multiple lines in said array, and wherein said sensor is scanned by pixel line so that effects of ambient light during scanning of said second frame are smeared throughout sequential pixel lines scanned from said sensor.

16. The apparatus set forth in claim 15 wherein said means for comparing said images comp rises means for comparing each signal from each pixel in each line scanned from said sensor to the same pixel signal from the next line scanned from said sensor so as to minimize effects of ambient light during said second frame.

17. The apparatus set forth in claim 8 wherein said first light source comprises an LED light source, and said second light source comprises a laser line light source.

18. The apparatus set forth in claim 8 wherein said light sensor comprises a frame transfer CCD sensor.

19. A method of inspecting a container for variations that affect commercial acceptability of the container, comprising the steps of:

(a) alternately directing first and second light energies of different character into a portion of the container, (b) obtaining first and second two-dimensional images of the portion of the container illuminated in said step (a) during illumination by said first and second light energies respectively, and (c) detecting commercial variations at the container that affect optical properties of the container by comparison of said first and second images to each other, wherein said step (b) comprises The steps of: (b1) directing said first and second light energies alternately into a single area array sensor to develop two-dimensional images of the illuminated portion of the container at said sensor and (b2) scanning said two-dimensional images from said sensor, and wherein said step (b2) is carried by: (b2a) controlling said sensor in sequential scan frames of equal time duration (b2b) directing said first and second light energies into the container during sequential first and second scan frames at said sensor, and (b2c) scanning said sensor during said first and second scan frames to obtain said two-dimensional images.

20. The method set forth in claim 19 wherein said step of comparing said images is carried out by overlapping said images.

21. The method set forth in claim 19 wherein said step (a) comprises the steps of: (a1) strobing a first light source to direct said first light energy into the container during said first frame, and (a2) strobing a second light source to direct said second light energy into the container during said second frame.

22. The method set forth in claim 21 wherein said first light source is strobed at an end of said first frame and said second light source is strobed at a beginning of said second frame.

23. The method set forth in claim 21 wherein said area array sensor has a plurality of individual sensor pixels adapted to integrate light energy incident thereon, and to provide pixel signals as a function of such integrated light energy, and wherein said step (b) comprises the additional step of: (b3) controlling pixel integration during at least one of said first and second frames so as to reduce effects of ambient light during pixel integration.

24. The method set forth in claim 23 wherein said first light source is strobed in said step (a1) at an end of said first frame, and said sensor is controlled in said step (b3) to integrate light energy from said first source at the end of said first frame.

25. The method set forth in claim 24 wherein said second light source is strobed in said step (a2) at an end of said second frame, and said sensor is controlled in said step (b3) to integrate light energy from said second source at the end of said second frame.

26. The method set forth in claim 24 wherein said second light source is strobed in said step (a2) at a beginning of said second frame, and said sensor is controlled in said step (b3) to integrate light energy from said second source during the entirety of said second frame.

27. The method set forth in claim 26 wherein said pixels are disposed in multiple lines in said array, and wherein said sensor is scanned in said step (b2c) by pixel line so that effects of ambient light during scanning of said second frame are smeared throughout sequential pixel lines scanned from said sensor.

28. The method set forth in claim 27 wherein said step (c) comprises the step of comparing each signal from each pixel in each line scanned from said sensor to the same pixel signal from the next line scanned from said sensor so as to reduce effects of ambient light during said second frame.

29. A method of inspecting a sealing surface of a container for variations that affect commercial acceptability of the container, comprising the steps of;

(a) alternately directing first and second light energies of different character into the sealing surface of the container, (b) obtaining first and second two-dimensional images of the sealing surface of the container illuminated in said step (a) during illumination by said first and second light energies respectively, and (c) detecting commercial variations at the container sealing surface that affect optical properties of the container sealing surface by comparison of said first and second images to each other, wherein said step (b) comprises the steps of: (b1) directing said first and second light energies alternately into a single area array sensor to develop two-dimensional images of the illuminated sealing surface of the container at said sensor, and (b2) scanning said two-dimensional images from said sensor, and wherein said first light source is such as to obtain at said sensor a two-dimensional image of light energy reflected from the sealing surface against a dark background, and said second light source is such as to obtain at said sensor a two-dimensional image of light energy reflected from high points at said sealing surface against a dark background.

* * * * *